United States Patent [19]

Robin

[11] Patent Number: 4,675,401

[45] Date of Patent: Jun. 23, 1987

[54] PROCESS FOR PREPARING POLYISOCYANATO/POLYISOCYANURATES BY CATALYTIC CYCLOTRIMERIZATION OF POLYISOCYANATES

[75] Inventor: Jean Robin, Lyons, France

[73] Assignee: Rhone-Poulenc Specialites Chimiques, Courbevoie, France

[21] Appl. No.: 792,835

[22] Filed: Oct. 30, 1985

[30] Foreign Application Priority Data

Oct. 30, 1984 [FR] France .............................. 84 16777

[51] Int. Cl.$^4$ .................. C07D 251/34; C08G 18/02; C08F 4/16
[52] U.S. Cl. ................................ 544/193; 544/222; 521/128; 521/902; 526/194; 528/52
[58] Field of Search ............... 544/222, 193; 521/128, 521/902; 526/194; 528/52

[56] References Cited

U.S. PATENT DOCUMENTS 4,537,961  8/1985  Robin .............................. 544/222

Primary Examiner—John M. Ford
Assistant Examiner—J. G. Mullins
Attorney, Agent, or Firm—Burns, Doane, Swecker & Mathis

[57] ABSTRACT

Polyisocyanurate/polyisocyanates of enhanced stability are prepared by partial catalytic cyclotrimerization of a polyisocyanate in the presence of a catalytically effective amount of an aminosilyl catalyst and wherein the cyclotrimerization reaction is terminated when a predetermined desired amount of isocyanurate groups has been attained, by adding to the reaction mixture, after the cooling thereof to a temperature of below 50° C., a reaction terminating amount of an organic catalyst deactivating compound comprising at least one free hydroxyl moiety, or the reaction product of such hydroxylated organic catalyst deactivating compound with an isocyanate.

7 Claims, No Drawings

PROCESS FOR PREPARING POLYISOCYANATE/POLYISOCYANURATES BY CATALYTIC CYCLOTRIMERIZATION OF POLYISOCYANATES

BACKGROUND OF THE INVENTION

1. Field of the Invention:

The present invention relates to an improved process for preparing polyisocyanurate/polyisocyanates via the partial catalytic cyclotrimerization of polyisocyanates, with the reaction being subsequently stopped at will when the trimer content thereof reaches the desired or predetermined value. More particularly, the present invention relates to an improved technique for deactivating the catalyst employed in the aforesaid process, when the catalyst comprises a compound which includes an aminosilyl function.

2. Description of the Prior Art:

In French Pat. No. 82/03799, published under No. 2,522,667 and published European Patent Application No. 0,089,297 (U.S. Pat. No. 4,537,961), a process is described for preparing polyisocyanurate/polyisocyanates by catalytic cyclotrimerization of polyisocyanates, using catalyst compounds containing aminosilyl groups, according to which, when the desired content in isocyanate groups is reached, the catalyst is destroyed by addition of a deactivating compound selected from among organic compounds (A) bearing at least one hydroxyl group, or the compounds resulting from the reaction of an isocyanate group with said organic compound (A), the organic compounds (A) optionally bearing substituent groups or atoms which are inert towards isocyanate groups, and said compounds including enols, alcohols, phenols, oximes or hydroxysilylated compounds.

The addition of the deactivator, or deactivating compound, is generally performed at a temperature between 50° and 180° C., preferably between 80° and 130° C., and especially at the temperature of cyclotrimerization. Cf. U.S. Pat. No. 3,992,316.

It has now surprisingly been found that the deactivation of the cyclotrimerization catalysts can advantageously be carried out at a temperature below 50° C., in the case where organic compounds bearing at least one hydroxyl group are employed as the deactivator. It has even been established, unexpectedly, that polyisocyanurate/polyisocyanates obtained in this manner show a further improvement in stability relative to those obtained according to the process of French Pat. No. 82/03799. This improved stability is manifested by the inability of the polyisocyanurates obtained by the process of the present invention to generate monomeric diisocyanate during storage, and even during heating for an extended period of time at a temperature greater than or equal to 50° C. It is especially important to avoid the presence of monomeric diisocyanates in polyisocyanurates, which are used in particular for producing coatings, the toxicity of which monomeric diisocyanates being well known.

SUMMARY OF THE INVENTION

Accordingly, a major object of the present invention is the provision of an improved process for preparing polyisocyanurate/polyisocyanates by catalytic cyclotrimerization of polyisocyanates, using as catalysts compounds containing aminosilyl groups, and then, when the desired content of isocyanate groups is reached, destroying the catalyst by adding to the reaction medium a deactivating compound selected from among organic compounds bearing at least one hydroxyl group and optionally groups or atoms which are inert towards isocyanates, and which improved process features addition of the deactivator at a temperature below 50° C.

The temperature at which the deactivating agent can be added to the reacting mass can be any value below 50° C. Although this temperature may be as low as −20° C., it is, from a practical point of view, of no value to carry out the addition of the deactivator at a temperature below 10° C. As a general rule, the temperature at which the deactivator is added preferably ranges from 15° to 40° C.

DETAILED DESCRIPTION OF THE INVENTION

More particularly according to the present invention, the organic compounds containing at least one hydroxyl group which are suitable as deactivators according to this invention are those noted in French Pat. No. 82/03799 and European Patent Application No. 0,089,297 (U.S. Pat. No. 4,537,961). More specifically, enols, primary, secondary or tertiary alcohols, primary, secondary or tertiary polyols, phenols, polyphenols, oximes, compounds containing hydroxysilyl groups such as silanols, silanediols, siloxanes or polysiloxanes containing hydroxysilyl group(s) are used. Of course, as above mentioned, in addition to the hydroxyl group, the compound (A) can optionally contain any other group or atom which is inert vis-a-vis isocyanate groups, such as ester, ether or amide groups, or organometallic or organometalloid groups.

Exemplary of the enols, compounds having at most 10 carbon atoms are representative, such as $\beta$-diketones, $\beta$-keto esters and $\beta$-cyano esters. Illustrative are acetylacetone, ethyl, methyl or pentyl acetoacetate and ethyl cyanoacetate.

Exemplary of the monoalcohols, primary, secondary or tertiary carbinols, having, in general, from 1 to 8 carbon atoms, are representative. These alcohols can optionally contain substituents which are inert towards isocyanate groups, such as ether, ester or amide groups. These alcohols can thus be hydroxyorganosilanes or hydroxyalkylsilanes. Such compounds will again be referred to in the description to follow.

Advantageously, if it is desired to completely remove the residue or remainder of the deactivator, "simple", purely hydrocarbon primary or secondary monoalcohols containing a small number of carbon atoms (at most 6 carbon atoms), such as methanol, ethanol, propanol, n-butanol, isopropanol or secondary butanol, etc., will be used within the scope of the process of the present invention. Preferably, primary or secondary monoalcohols having from 3 to 6 carbon atoms, and the volatility of which is thereby not too great, such as butanol or isopropanol, will be used.

As the organic compound (A), a polyol, optionally substituted by one or more inert groups as defined above, can also be used. In such a context, the following are representative:

(i) Glycerol,
(ii) 1,3-Propylene glycol,
(iii) 1,4-Butanediol,
(iv) Triethylene glycol,
(v) 1,3-Octanediol,
(vi) 1,4-Butynediol, (vii) Trimethylolpropane,
(viii) Diethylene glycol monoethyl or methyl ether (Diglyme).

The polyols advantageously have from 2 to 12 carbon atoms and preferably from 2 to 8 carbon atoms.

The phenols which can be used can be mono- or polycyclic phenols optionally containing one or more phenol groups, and can also contain various substituents which are inert towards isocyanate groups, such as alkyl, ester or ether groups, or halogen atoms. By way of example, the following are representative of the phenols which can be used:
(i) Phenol,
(ii) Cresols,
(iii) Xylenols,
(iv) Nonylphenol,
(v) Tert-butylphenols,
(vi) Dihydroxybenzene,
(vii) 4,4'-Dihydroxybiphenyl,
(viii) 4,4'-Dihydroxydiphenylmethane,
(ix) Hydroxynaphthalene,
(x) Naphthalenediol.

The oximes which can be used include ketoximes or aldoximes, obtained by reaction of hydroxylamine with linear or cyclic aldehydes or ketones having at most 10 carbon atoms, and exemplary of such oximes are acetone oxime, methyl ethyl ketone oxime, cyclohexanone oxime, 2-hexanone oxime and cinnamaldehydeoxime.

Among the compounds containing hydroxysilyl groups, the following are representative:
(i) Trimethylsilanol,
(ii) Dimethylsilanediol,
(iii) Triethylsilanol,
(iv) Diethylsilanediol,
(v) Triphenylsilanol,
(vi) Diphenylsilanediol,
(vii) Dihydroxydimethyldisiloxane,
(viii) Dihydroxydiphenyldisiloxane,
(ix) Bis-$\alpha,\omega$-dihydroxy(octaphenyltetrasiloxane).

Organosilicon compounds bearing hydroxyl groups not directly attached to a silicon atom can, of course, be used in the context of the present invention. It is thus possible to use hydroxyorganosilanes or hydroxyorganopolysiloxanes, such as:
(i) Trimethyl(hydroxymethyl)silane,
(ii) (Hydroxybutyl)trimethylsilane,
(iii) Bis(hydroxypropyl)dimethylsilane,
(iv) Hydroxyphenyltrimethylsilane.

The organosilicon compounds containing hydroxyl groups are, for example, described in the text by Walter Noll, *Chemistry and Technology of Silicones,* English edition (1968).

Advantageously, it is preferred to use within the scope of the present invention, a primary or secondary monoalcohol having from 3 to 6 carbon atoms. Use of butanol or isopropanol proves to be especially suitable.

The amount of deactivating agent employed can vary. It is not critical but will, of course, depend upon the amount of catalyst initially introduced into the polyisocyanate.

In general, the amount of deactivating agent is such that the mole ratio between the deactivating agent and the catalyst ranges from 0.5 to 2, and preferably from 0.8 to 1.5. A molar ratio on the order of 1 is advantageously used.

The aminosilyl compounds used as cyclotrimerization catalysts in the process according to the invention are those described in European Patent Applications Nos. 0,057,653 and 0,089,297 (U.S. Pat. No. 4,537,961), namely, the compounds having the formula (I):

in which the various symbols denote, respectively:

R: a monovalent hydrocarbon radical, aliphatic, cycloaliphatic, saturated or unsaturated, aryl, aralkyl or alkylaryl, optionally substituted with halogen atoms or CN groups, with the proviso that two of the radicals R may together form a single divalent hydrocarbon radical;

R': a monovalent radical selected from among the radicals R, SiR$_3$, or amide radicals of the formula:

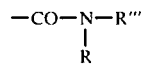

R'''denoting R or SiR$_3$, with R being as above defined, with the proviso that the radical R', when it is not an amide group or an SiR$_3$ group, may form, together with the radical R'', a single divalent hydrocarbon radical;

R'': a monovalent radical having the same definition as the radical R; or a hydrogen atom when R' is not an amide radical;

n: an integer equal to 1 or 2. When n equals 2, R' is a radical R.

The catalyst, which can be an aminosilane, diaminosilane, silylurea or silazane is more preferably a compound of the formula (I) in which the various symbols denote, respectively:

R: an alkyl, alkenyl or haloalkyl or haloalkenyl radical having from 1 to 5 carbon atoms and containing from 1 to 6 chlorine and/or fluorine atoms, a cycloalkyl, cycloalkenyl or halocycloalkyl radical, a halocycloalkenyl radical having from 5 to 8 carbon atoms and containing from 1 to 4 chlorine and/or fluorine atoms, an aryl, alkylaryl or haloaryl radical having from 6 to 8 carbon atoms and containing from 1 to 4 chlorine and/or fluorine atoms, or a cyanoalkyl radical having from 3 to 4 carbon atoms, with the proviso that two R's borne by the same silicon atom may together form a single divalent radical having from 1 to 4 carbon atoms;

R': a monovalent radical selected from among the radicals R, SiR$_3$ and CO(NR)—R''', with R''' denoting R or SiR$_3$, with R being immediately above defined, with the proviso that R' and R'' may together form a single alkylene radical having from 4 to 6 carbon atoms;

R'': an alkyl or alkenyl radical having from 1 to 4 carbon atoms, a cycloalkyl or cycloalkenyl radical having from 4 to 6 ring carbon atoms, a phenyl, tolyl or xylyl radical, or a hydrogen atom when R' is not an amide group.

The aminosilyl compounds of the formula (I) which are preferably used as cyclotrimerization catalysts are those of the above formula in which the various symbols respectively represent the following:

R: a methyl, ethyl, propyl, vinyl or phenyl radical, such radicals optionally being chlorinated and/or fluorinated;

R': an alkyl radical selected from among methyl, ethyl, propyl or butyl radicals, a radical SiR$_3$, with R being as above defined, a carboxamide radical of one of the formulae:

with R also being as above defined;
R'': a methyl, ethyl, propyl or butyl radical, or a hydrogen atom.

Also, R' and R'' may together form a butylene or pentylene radical.

As above mentioned, the cyclotrimerization catalyst can be an aminosilane, diaminosilane, monosilylurea, disilylurea or silazane. It is a simple matter to determine the exact chemical nature of the various compounds having aminosilyl groups which can be used, given the various definitions for the several radicals R, R', R'', R'''. It will be seen, in particular, that the use of silylurea obtained by reaction of a secondary amine and N-silyl isocyanates is not envisaged. These silylureas are unsuitable in the catalytic cyclotrimerization process since they liberate or release the silylisocyanate on heating.

Compounds containing an aminosilyl group will be an aminosilane where n equals 1 and R' represents a radical R, with the radicals R and R'' being as defined above, with the proviso that two radicals R may together form a single divalent radical or, alternatively, R' and R'' may also together form a single divalent radical.

Exemplary of the aminosilanes, the following are representative:
(i) Methylaminotrimethylsilane,
(ii) Dimethylaminotrimethylsilane,
(iii) Diethylaminotrimethylsilane,
(iv) Dibutylaminotrimethylsilane,
(v) Diethylaminodimethylvinylsilane,
(vi) Diethylaminodimethylphenylsilane.

The compound having an aminosilyl group will be a diaminosilane when n equals 2 and R' denotes the radical R, with the radicals R and R'' being as above defined and with the proviso that two radicals R may together form a single divalent radical or, alternatively, R' and R'' may also together form a single divalent radical.

Exemplary of diaminosilanes, the following are representative:
(i) Bis(dimethylamino)dimethylsilane,
(ii) Bis(dibutylamino)dimethylsilane,
(iii) Bis(dimethylamino)methylphenylsilane.

The compound having an aminosilyl group will be a silylurea when n equals 1 and R' represents a carboxamide group

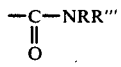

in which R''' represents a radical R or SiR$_3$, with the radicals R and R'' being as above defined, and with the proviso that two radicals R may together form a single divalent radical, or the two radicals R' and R'' (R' then representing R) may also together form a single divalent radical. Exemplary of the silylureas, the following are representative:
(i) N-Methyl-N-trimethylsilyl-N'-methyl-N'-butylurea,
(ii) N-Trimethylsilyl-N-methyl-N',N'-dimethylurea,
(iii) N-Trimethylsilyl-N-ethyl-N',N'-dimethylurea,
(iv) N-Trimethylsilyl-N-butyl-N'-butyl-N'trimethylsilylurea.

The compounds having an aminosilyl group will be a silazane when n equals 1 and R' represents an SiR$_3$ group.

The silazanes can be symmetrical or asymmetrical; symmetrical disilazanes are preferably employed, with the two SiR$_3$ groups being identical.

Exemplary of the disilazanes which can be used, the following are representative:
(i) Hexamethyldisilazane,
(ii) Heptamethyldisilazane,
(iii) 1,3-Diethyl-1,1,3,3-tetramethyldisilazane,
(iv) 1,3-Divinyl-1,1,3,3-tetramethyldisilazane,
(v) Hexamethyldisilazane,
(vi) 1,3-Diphenyl-1,1,3,3-tetramethyldisilazane.

Finally, among the disilazanes, hexamethyldisilazane and heptamethyldisilazane, which prove to be the most especially advantageous catalysts, are the most preferred.

In the process of the present invention, any simple or adduct polyisocyanate of aliphatic, cycloaliphatic or aromatic type can be cyclotrimerized to give a polyisocyanurate/polyisocyanate, provided that the catalyst compound containing an aminosilyl group is the appropriate one for this particular reaction.

Thus, the catalytic cyclotrimerization of simple polyisocyanates or polyisocyanate adducts, the isocyanate groups of which are not directly linked to an aromatic ring, can easily be carried out using, as the catalyst, an aminosilane, a diaminosilane, a silylurea or a silazane, as hereinbefore described.

In this respect, exemplary of the aliphatic or cycloaliphatic diisocyanates, representative are:
(i) Tetramethylene diisocyanate,
(ii) Pentamethylene diisocyanate,
(iii) Hexamethylene diisocyanate,
(iv) 1,2-Diisocyanatocyclohexane,
(v) 1,4-Diisocyanatocyclohexane,
(vi) 1,2-Bis(isocyanatomethyl)cyclobutane,
(vii) Bis(4-isocyanatocyclohexyl)methane,
(viii) 3,3,5-Trimethyl-5-isocyanatomethyl-1-isocyanatocyclohexane.

Among these, especially preferred is hexamethylene diisocyanate.

Finally, among adduct or prepolymeric polyisocyanates which can be used as aliphatic polyisocyanates, exemplary are the modified polyisocyanates which are obtained by reacting an excess of aliphatic or cycloaliphatic polyisocyanate with a compound containing at least two groups which are reactive with isocyanate groups, such as a diamine or diacid. The modified polyisocyanates, which can be mixed with simple polyisocyanates, can contain urea, biuret, ester or siloxane groups.

Within the scope of the process of the present invention, any simple or adduct polyisocyanate of aromatic type, namely, those in which the NCO group is directly linked to an aromatic group, can also be cyclotrimerized to polyisocyanurate/polyisocyanate. To achieve this, aminosilanes, diaminosilanes or silylureas, as described above, will be used as the catalysts bearing aminosilyl functions.

Exemplary of the aromatic diisocyanates which can be used, the following are representative:
(i) 1,4-Diisocyanatobenzene,
(ii) Diisocyanatotoluene (2,4- and 2,6-, or, alternatively, mixtures thereof),
(iii) 4,4'-Diisocyanatodiphenylmethane,
(iv) 4,4'-Diisocyanatodiphenyl ether, (v) Polymethylene and polyphenylene polyisocyanates.

Any adduct polyisocyanate resulting from the polycondensation of an excess of polyisocyanate with a polyfunctional compound, such as a diamine or diacid, can also be used as the aromatic polyisocyanate. The modified polyisocyanates which can be mixed with simple polyisocyanates can contain urea, biuret, ester or siloxane groups.

The amount of catalytic agent introduced into the isocyanate can vary widely; it typically ranges from 0.1 to 10%, and preferably from 0.5 to 5%, expressed by weight relative to the isocyanate. Small additional amounts of catalyst can optionally be introduced over the course of the reaction.

The cyclotrimerization process to give polyisocyanurate/polyisocyanate can be carried out by simply heating the reactants to a temperature which typically ranges from 50° C. to 180° C., preferably from 80° C. to 130° C. and customarily around 100° C.

It is also possible, where appropriate, to carry out the cyclotrimerization reaction in a solvent medium, the latter advantageously a solvent of low polarity such as, for example, an aliphatic or aromatic hydrocarbon, or an ester or ether. The catalyst can then be introduced into the solvent and this solution introduced into the isocyanate. It is, of course, also possible to introduce the catalytic solution into the isocyanate. Advantageously, the process is carried out without a solvent.

When the isocyanurate content reaches the desired value, the temperature of the reacting mass is lowered to a value below 50° C., and the deactivator, the nature and amount of which have been described above, is added.

The excess monomeric polyisocyanate can then be optionally removed by any known means, and a polyisocyanurate/polyisocyanate is produced which has a highly reduced monomeric isocyanate content, as well as a small amount of dimeric isocyanate.

The polyisocyanurate/polyisocyanates, such as those derived from hexamethylene diisocyanate, are well known compounds which are especially useful as base constituents for varnishes and paints.

In order to further illustrate the present invention and the advantages thereof, the following specific examples are given, it being understood that same are intended only as illustrative and in nowise limitative.

EXAMPLE 1

Into a 3-liter round-bottomed flask equipped with a stirrer and thermometer, 2,400 g of 1,6-diisocyanatohexane were charged. The compound was heated on a waterbath to 95° C., and 48 g of hexamethyldisilazane were then added; the temperature was maintained at 100° for 2 h 15 min. At that moment, an NCO group content of 0.990/100 g was assayed. The reacting mass was then divided into three equal portions A, B and C.

Portion A: The temperature was maintained at 100°, 8 g of n-butanol were added and the mixture was then allowed to cool. A small amount (10 to 20 g) was maintained for 20 hr at 100°, to confirm that the trimerization had indeed stopped. After this period of time, the NCO group content and viscosity did not change relative to the values measured at the point in time of arresting the reaction.

The remainder of A was then evaporated by means of an agitated film layer evaporator, until a trimer was obtained which no longer contained free diisocyanate (content less than or equal to 0.1% by weight). The trimer A' was thereby obtained.

Portion B: This was cooled rapidly to 30° and 8 g of n-butanol were added. As above, it was verified on a small amount that the trimerization had indeed stopped; after 20 hr at 100°, the NCO group content remained constant. The remainder of the fraction B was then evaporated as for A, and gave the trimer B' containing less than 0.1% by weight of free diisocyanate.

Portion C: This was cooled rapidly to 5° and 8 g of n-butanol were then added thereto. The procedure was as for B:

(a) it was established on a sample of this portion C that stopping of the trimerization was effective (NCO content unchanged after 20 hr at 100°);

(b) the remainder was evaporated and the trimer c' obtained, containing at most 0.1% of free diisocyanate.

The fractions A', B' and C' were stored at room temperature. Their stability was measured by withdrawing the sample and maintaining it for 60 days at 60°, its free diisocyanate content then being determined. It was established that, for A', this content reached 0.6% by weight, whereas it remained virtually unchanged for B' and C' (less than 0.2% by weight).

EXAMPLE 2

The trimerization of diisocyanatohexane was commenced as described in Example 1.

When the NCO group content was 0.975 per 100 g, the mixture was cooled rapidly to 30°. The reacting mass was divided into 5 equal portions: D, E, F, G, H.

Respectively to each of these fractions, 0.06 mole of the following was added:

(i) Isopropanol: (fraction D)
(ii) 2-Methylpropanol: (fraction E)
(iii) Trimethylsilanol: (fraction F)
(iv) Phenol: (fraction G)
(v) Ethylene glycol: (fraction H).

A small amount of each of these fractions was maintained for 20 hr at 100°; it was established that effective stopping of the reaction had indeed been achieved, since the NCO content hardly changed. These five fractions were evaporated as in Example 1, until the corresponding trimers D', E', F', G' and H' were obtained, the free isocyanate content of which was less than or equal to 0.1% by weight.

After storage at 60° for 60 days, the content by weight of free isocyanate remained virtually unchanged (less than 0.2% by weight).

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a polyisocyanatopolyisocyanurate by the catalytic cyclotrimerization of an aliphatic or cycloaliphatic polyisocyanate in the presence of a catalytically effective amount of an aminosilyl catalyst and wherein the cyclotrimerization reaction is terminated when a predetermined desired amount of isocyanurate groups has been attained, by adding to the reaction mixture a reaction terminating amount of an organic catalyst deactivating compound comprising at least one free hydroxyl moiety, or the reaction product of such hydroxylated organic catalyst deactivating compound with an isocyanate, the improvement which comprises adding said catalyst deactivating compound to said reaction mixture after the temperature thereof has been cooled to a temperature of below 50° C.

2. The process as defined by claim 1, comprising adding said catalyst deactivating compound to said reaction mixture after the temperature thereof has been cooled to a temperature of from 15° to 40° C.

3. The process as defined by claim 1, said catalyst deactivating compound comprising an enol, alcohol, polyol, phenol, polyphenol, ketoxime, or hydroxysilylated organosilicon compound.

4. The process as defined by claim 3, said catalyst deactivating compound comprising a primary or secondary monoalcohol having from 1 to 8 carbon atoms.

5. The process as defined by claim 4, said monoalcohol having from 3 to 6 carbon atoms.

6. The process as defined by claim 1, wherein the amount of catalyst deactivating compound added, expressed in moles per mole of catalyst, ranges from 0.5 to 2.

7. The process as defined by claim 1, wherein said aminosilyl cyclotrimerization catalyst comprises an aminosilane, diaminosilane, monosilylurea, disilylurea or silazane.

* * * * *